United States Patent
Cahoon et al.

(10) Patent No.: US 6,600,089 B1
(45) Date of Patent: Jul. 29, 2003

(54) CAROTENOID BIOSYNTHESIS ENZYMES

(75) Inventors: Rebecca E. Cahoon, Wilmington, DE (US); Anthony J. Kinney, Wilmington, DE (US); Steven J. Vollmer, Wilmington, DE (US); Zude Weng, Des Plaines, IL (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/690,942

(22) Filed: Oct. 18, 2000

Related U.S. Application Data

(63) Continuation-in-part of application No. PCT/US99/08746, filed on Apr. 21, 1999.
(60) Provisional application No. 60/083,042, filed on Apr. 24, 1998.

(51) Int. Cl.$^7$ .......................... A01H 3/00; C07H 21/04; C12N 5/14; C12N 9/00

(52) U.S. Cl. .......................... 800/278; 435/6; 435/69.1; 435/70.1; 435/183; 435/410; 435/419; 435/252.3; 435/320.1; 530/350; 530/370; 536/23.2; 536/23.6; 536/24.1; 800/295

(58) Field of Search .......................... 435/6, 69.1, 70.1, 435/183, 410, 419, 252.3, 320.1; 530/350, 370; 536/23.2, 23.6, 24.1; 800/278, 295

(56) References Cited

FOREIGN PATENT DOCUMENTS

| WO | 95/34668 | 12/1995 |
| WO | 98/06862 | 2/1998 |

OTHER PUBLICATIONS

EMBL Sequence Library Accession No.: U38550, Nov. 10, 1995, Scolnik, P.A. Et Al., Nucleotide Sequence of Zeta–carotene desaturase from Arabidopsis.
EMBL Sequence Library Accession No.: AJ224683, Mar. 2, 1998, Al–Babili, S., Evidence for Multiple copies of Formate Dehydrogenase Genes in Plants: Isolation of Three Potato fdh Genes, fdh1, fdh2, and fdh3.
EMBL Sequence Library Accession No.: C27136, Aug. 6, 1997, Yamamoto, K. Et Al., Rice cDNA from Callus.
Manuela Albrecht Et Al., European J. Biochem., vol. 236: 115–120, 1996, Biochemical Characterization of Purified beta–carotene desaturase from Anabaena PCC 7120 after Expression in escherichia Coli.
Gerhard Sandmann Et Al., Zeitschrift Fur Naturforschung, vol. 51:534–538, Jul. 1996, A New Non–Radioactive Assay of Phytoene Desaturase to Evaluate Bleaching Herbicides.
Jurgen Breitenbach Et Al., Plant Molecular Biology, vol. 36:725–732, 1998, A Higher–Plant Type beta–carotene Desaturase in the Cyanobacterium Synechocystis PCC6803.
Glenn E. Bartley Et Al., PNAS, vol. 88:6532–6536, Aug. 1991, Molecular Cloning and Expression in Photosynthetic Bacteria of a Soybean cDNA Coding For Phytoene Desaturase, an Enzyme of the Carotenoid Biosynthesis Pathway.
EMBL Sequence Library Accession No.: AI495658, Mar. 17, 1999, Shoemaker, R. Et Al., Public Soybean ESt Project.
EMBL Sequence Library Accession No.: AF047490, Jan. 6, 1999, Luo, R. Et Al.
EMBL Sequence Library Accession No.: AF049356, Jan. 6, 1999, Vigneswaran, A. Et Al., Isolation of Rice Phytoene Desaturase cDNA.
Glenn E. Bartley Et Al., Plant Cell, vol. 7:1027–1038, Jul. 1995, Plant Carotenoids: Pigments for Photoprotection, Visual Attraction, and Human Health.
M. L. Scott Et Al., Poultry Science, vol. 47:863–872, 1968, Studies of Egg Yolk Pigmentation.
National Center for Biotechnology Information General Identifier No. 2924362, Jul. 17, 1998, Al–Babili, S.
Hourton–Cabassa, C. Et Al., Plant Phys., vol. 117:719–, 1998, Evidence for Multiple Copies of Formate Dehydrogenase Genes in Plants: Isolation of Three Potato fdh Genes, fdh1, fdh2, and fdh3.
National Center for Biotechnology Information General Identifier No. 1583601, Oct. 28, 1996, Albrecht, M. Et Al., Molecular Cloning and Functional Expression in E. coli of a Novel Plant Enzyme Mediating Zeta–Carotene Desaturation.
Manuela Albrecht Et Al., FEBS Letters, vol. 372:199–292, 1995, Molecular Cloning and Functional Expression in E. coli of a Novel Plant Enzyme Mediating Zeta–Carotene Desaturation.
National Center for Biotechnology Information General Identifier No. 4105563, Aug. 25, 1999, Luo, R. Et Al.
National Center for Biotechnology Information General Identifier No. 2129927, Jul. 21, 2000, Albrecht, M. Et Al., Molecular Cloning and Functional Expression in E. coli of a Novel Plant Enzyme Mediating Zeta–Carotene Desaturation.
National Center for Biotechnology Information General Identifier No. 2707976, Apr. 7, 1998, Wurtzel, E.T., Use of a Ds Chromosome Breaking Element to Examine Maize Vp5 Expression.
Wurtzel, E. T., Journ. of Hered., vol. 83:109–113, 1992, Use of a Ds Chromosome Breaking Element to Examine Maize Vp5 Expression.

(List continued on next page.)

*Primary Examiner*—Phuong T. Bui

(57) ABSTRACT

This invention relates to an isolated nucleic acid fragment encoding a carotenoid biosynthetic enzyme. The invention also relates to the construction of a chimeric gene encoding all or a portion of the carotenoid biosynthetic enzyme, in sense or antisense orientation, wherein expression of the chimeric gene results in production of altered levels of the carotenoid biosynthetic enzyme in a transformed host cell.

10 Claims, No Drawings

OTHER PUBLICATIONS

Zhou–Hui Et Al., Plant Mol. Biol., vol. 30:269–279, 1996, Cloning and Characterization of a Maize cDNA Encoding Phytoene Desaturase, an Enzyme of the Carotenoid Biosynthetic Pathway.

National Center for Biotechnology Information General Identifier No. 780270, Apr. 11, 1997, Al–Babili, S Et Al., A Novel, Soluble Form of Phytoene Desaturase from Narcissus Pseudonarcissus Chromoplasts is Hsp70–complexed and Competenet for Flavinylation, Membrane Association and Enzymatic Activation.

Salim Al–Babili Et Al., Plant J. vol. 9(5):601–612, 1996, A Novel, Soluble Form of Phytoene Desaturase from Narcissus Pseudonarcissus Chromoplasts is Hsp70–complexed and Competenet for Flavinylation, Membrane Association and Enzymatic Activation.

Al–Babili, S. Et Al., Plant Phys., vol. 110:337, 1995, A cDNA Encoding Phytoene Desaturase from Daffodil.

National Center for Biotechnology Information General Identifier No. 1345838, Jul. 15, 1999, Cloning a Characterization of a Maize cDNA Encoding Phytoene Desaturase, an Enzyme of the Carotenoid Biosynthetic Pathway.

Hartmut Linden Et Al., Plant Mol. Biol. vol. 24:369–379, 1994, A Novel Carotenoid Biosynthesis Gene Coding for – carotene Desaturase: Functional Expression, Sequence and Phylogenetic Origin.

Iris Pecker Et Al., PNAS, vol. 89:4962–4966, Jun. 1992, A Single Polypeptide Catalyzing the Conversion of Phytoene to –Carotene is Transcriptionally Regulated During Tomoto Fruit Ripening.

CAROTENOID BIOSYNTHESIS ENZYMES

This application is a continuation-in-part of Application No. PCT/US99/08746 filed Apr. 21, 1999, now pending, which claims priority benefit of U.S. Provisional Application No. 60/083,042, filed Apr. 24, 1998.

FIELD OF THE INVENTION

This invention is in the field of plant molecular biology. More specifically, this invention pertains to nucleic acid fragments encoding enzymes of the carotenoid biosynthesis pathway in plants and seeds.

BACKGROUND OF THE INVENTION

Plant carotenoids are orange and red lipid-soluble pigments found embedded in the membranes of chloroplasts and chromoplasts. In leaves and immature fruits the color is masked by chlorophyll but in later stages of development these pigments contribute to the bright color of flowers and fruits. Carotenoids protect against photoxidation processes and harvest light for photosynthesis. The carotenoid biosynthesis pathway leads to the production of abscisic acid with intermediaries useful in the agricultural and food industries as well as products thought to be involved in cancer prevention. (Bartley, G. E., and Scolnik, P. A. (1995) *Plant Cell* 7:1027–1038).

Phytoene desaturase transforms phytoene to zeta carotene via phytofluene. cDNAs encoding this bifunctional enzyme have been identified from bacteria, peppers, corn, Arabidopsis and Narcissus. The lightly colored zeta-carotene is converted to neurosporene by the zeta-carotene desaturase enzyme (carotene 7, 8 desaturase; EC 1.134.99.30). cDNAs encoding zeta carotene desaturase have been identified in bacteria, corn, Narcissus, tomato, Arabidopsis and pepper. Neurosporene is further desaturated into lycopene. Lycopene may have one of two different fates: through the action of lycopene epsilon cyclase it may become alpha carotene, or it may be transformed into beta carotene by lycopene cyclase. Beta-carotene dehydroxylase converts beta-carotene into zeaxanthin. Zeaxanthin epoxidase transforms zeaxanthin into violxanthin and eventually absisic acid.

Zeaxanthin is the bright orange product highly prized as a pigmenting agent for animal feed which makes the meat fat, skin, and egg yolks a dark yellow (Scott, M. L. et al. (1968) *Poultry Sci.* 47:863–872). Gram per gram, zeaxanthin is one of the best pigmenting compounds because it is highly absorbable. Yellow corn, which produces one of the best ratios of lutein to zeaxanthin contains in average 20 to 25 mg of xanthophyll per kg while marigold petals yield 6,000 to 10,000 mg/kg.

SUMMARY OF THE INVENTION

The instant invention relates to isolated nucleic acid fragments encoding carotenoid biosynthetic enzymes. Specifically, this invention concerns an isolated nucleic acid fragment encoding a zeta carotene desaturase or a phytoene desaturase. In addition, this invention relates to a nucleic acid fragment that is complementary to the nucleic acid fragment encoding zeta carotene desaturase or phytoene desaturase.

An additional embodiment of the instant invention pertains to a polypeptide encoding all or a substantial portion of a carotenoid biosynthetic enzyme selected from the group consisting of zeta carotene desaturase and phytoene desaturase.

In another embodiment, the instant invention relates to a chimeric gene encoding a zeta carotene desaturase or a phytoene desaturase, or to a chimeric gene that comprises a nucleic acid fragment that is complementary to a nucleic acid fragment encoding a zeta carotene desaturase or a phytoene desaturase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a zeta carotene desaturase or a phytoene desaturase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a zeta carotene desaturase or a phytoene desaturase in a transformed host cell comprising: a) transforming a host cell with a chimeric gene comprising a nucleic acid fragment encoding a zeta carotene desaturase or a phytoene desaturase; and b) growing the transformed host cell under conditions that are suitable for expression of the chimeric gene wherein expression of the chimeric gene results in production of altered levels of zeta carotene desaturase or phytoene desaturase in the transformed host cell.

An addition embodiment of the instant invention concerns a method for obtaining a nucleic acid fragment encoding all or a substantial portion of an amino acid sequence encoding a zeta carotene desaturase or a phytoene desaturase.

A further embodiment of the instant invention is a method for evaluating at least one compound for its ability to inhibit the activity of a zeta carotene desaturase or a phytoene desaturase, the method comprising the steps of: (a) transforming a host cell with a chimeric gene comprising a nucleic acid fragment encoding a zeta carotene desaturase or a phytoene desaturase, operably linked to suitable regulatory sequences; (b) growing the transformed host cell under conditions that are suitable for expression of the chimeric gene wherein expression of the chimeric gene results in production of zeta carotene desaturase or phytoene desaturase in the transformed host cell; (c) optionally purifyring the zeta carotene desaturase or the phytoene desaturase expressed by the transformed host cell; (d) treating the zeta carotene desaturase or the phytoene desaturase with a compound to be tested; and (e) comparing the activity of the zeta carotene desaturase or the phytoene desaturase that has been treated with a test compound to the activity of an untreated zeta carotene desaturase or phytoene desaturase, thereby selecting compounds with potential for inhibitory activity.

SEQUENCE DESCRIPTIONS

The invention can be more fully understood from the following detailed description and the accompanying Sequence Listing which form a part of this application.

The following sequence descriptions and sequence listings attached hereto comply with the rules governing nucleotide and/or amino acid sequence disclosures in patent applications as set forth in 37 C.F.R. §1.821–1.825.

SEQ ID NO:1 is the nucleotide sequence comprising portion of the cDNA insert in clone rls6.pk0080.a9 encoding the N-terminal fifth of a rice zeta-carotene desaturase.

SEQ ID NO:2 is the deduced amino acid sequence of the N-terminal fifth of a rice zeta-carotene desaturase derived from the nucleotide sequence of SEQ ID NO:1.

SEQ ID NO:3 is the nucleotide sequence comprising a portion of the cDNA insert in clone rls6.pk0080.a9 encoding the C-terminal quarter of a rice zeta-carotene desaturase.

SEQ ID NO:4 is the deduced amino acid sequence of the C-terminal quarter of a rice zeta-carotene desaturase derived from the nucleotide sequence of SEQ ID NO:3.

SEQ ID NO:5 is the nucleotide sequence comprising a portion of the cDNA insert in clone sr1.pk0022.a12 encoding a portion of a soybean zeta-carotene desaturase.

SEQ ID NO:6 is the deduced amino acid sequence of a portion of a soybean zeta-carotene desaturase derived from the nucleotide sequence of SEQ ID NO:5.

SEQ ID NO:7 is the nucleotide sequence comprising the entire cDNA insert in clone wlm24.pk0031.e9 encoding an entire wheat zeta-carotene desaturase.

SEQ ID NO:8 is the deduced amino acid sequence of an entire wheat zeta-carotene desaturase derived from the nucleotide sequence of SEQ ID NO:7.

SEQ ID NO:9 is the nucleotide sequence comprising the entire cDNA insert in clone rlr6.pk0027.d5 encoding an entire rice phytoene desaturase.

SEQ ID NO:10 is the deduced amino acid sequence of an entire rice phytoene desaturase derived from the nucleotide sequence of SEQ ID NO:9.

SEQ ID NO:11 is the nucleotide sequence comprising the entire cDNA insert in clone wlm12.pk0003.g5 encoding a nearly entire wheat phytoene desaturase.

SEQ ID NO:12 is the deduced amino acid sequence of a nearly entire wheat phytoene desaturase derived from the nucleotide sequence of SEQ ID NO:11.

SEQ ID NO:13 is the amino acid sequence of a *Zea mays* zeta carotene desaturase, NCBI gi Accession No. 4105563.

SEQ ID NO:14 is the amino acid sequence of a *Capsicum annuum* zeta carotene desaturase, NCBI gi Accession No. 2129927.

SEQ ID NO:15 is the amino acid sequence of a *Zea mays* phytoene desaturase, NCBI gi Accession No. 1345838.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, the term isolated polynuceotide refers to a polynucleotide that is substacially free from other nucleid acid sequences, such as other chromosomal and extrachromosomal DNA and RNA that normally accompany or interact with the isolated polynucleotide as found in its naturally occurring environment. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar nucleic acid sequences encompassed by this invention are also defined by their ability to hybridize, under stringent conditions (0.1×SSC, 0.1% SDS, 65° C.), with the sequences exemplified herein. Preferred substantially similar amino acid fragments of the instant invention are those amino acid fragments whose protein sequences are 95% identical to the protein fragments reported herein. Sequence alignments and percent similarity calculations were performed using the Megalign program of the LASARGENE bioinformatics computing suite (DNASTAR Inc., Madison, Wis.). Multiple alignment of the amino acid sequences was performed using the Clustal method of alignment (Higgins, D. G. and Sharp, P. M. (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment that encodes all or a substantial portion of the amino acid sequence encoding the zeta carotene desaturase or the phytoene desaturase proteins as set forth in SEQ ID NOs:2, 4, 6, 8, 10 and 12. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native-gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) Meth. Enzymol. 143:277) and particle-accelerated or "gene gun" transformation technology (Klein T. M. et al. (1987) Nature (London) 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. Molecular Cloning. A Laboratory Manual; Cold Spring Harbor Laboratory Press: Cold Spring Harbor, 1989 (hereinafter "Maniatis").

Nucleic acid fragments encoding at least a portion of several carotenoid biosynthetic enzymes have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Carotenoid Biosynthetic Enzymes

| Enzyme | Clone | Plant |
| --- | --- | --- |
| Zeta Carotene Desaturase | rls6.pk0080.a9 | Rice |
|  | sr1.pk0022.a12 | Soybean |
|  | wlm24.pk0031.e9 | Wheat |
| Phytoene Desaturase | rlr6.pk0027.d5 | Rice |
|  | wlm12.pk0003.g5 | Wheat |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other zeta carotene desaturases or phytoene desaturases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the MRNA precursor encoding plant genes. Alternatively, the second primer sequence may be based upon sequences derived from the cloning vector. For example, the skilled artisan can follow the RACE protocol (Frohman et al., (1988) Proc. Natl. Acad. Sci. USA 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) Proc. Natl. Acad. Sci. USA 86:5673; Loh et al., (1989) Science 243:217). Products generated by the 3' and 5' RACE procedures can be combined to generate full-length cDNAs (Frohman, M. A. and Martin, G. R., (1989) Techniques 1: 165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) Adv. Immunol. 36:1; Maniatis).

The nucleic acid fragments of the instant invention may be used to create transgenic plants in which the disclosed zeta carotene desaturase or phytoene desaturase are present at higher or lower levels than normal or in cell types or developmental stages in which they are not normally found. This would have the effect of altering the level of lycopene and phytoene in those cells. Manipulation of the zeta carotene desaturase or phytoene desaturase levels in transgenic plants may allow a greater accumulation of lycopene, zeaxanthin and eventually absisic acid.

Overexpression of the zeta carotene desaturase or the phytoene desaturase proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) EMBO J. 4:2411–2418; De Almeida et al., (1989) Mol. Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant carotenoid biosynthetic enzymes to different cellular compartments, or to facilitate its secretion from the cell. It is thus envisioned that the chimeric gene described above may be further supplemented by altering the coding sequence to encode zeta carotene desaturase or phytoene desaturase with appropriate intracellular targeting sequences such as transit sequences (Keegstra, K. (1989) Cell 56:247–253), signal sequences or sequences encoding endoplasmic reticulum localization (Chrispeels, J. J., (1991) Ann. Rev. Plant Phys. Plant Mol. Biol. 42:21–53), or nuclear localization signals (Raikhel, N. (1992) Plant Phys. 100: 1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding zeta carotene desaturase or phytoene desaturase in plants for some applications. In order to accomplish this, a chimeric gene designed for co-suppression of the instant carotenoid biosynthetic enzyme can be constructed by linking a gene or gene fragment encoding a zeta carotene desaturase or a phytoene desaturase to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant zeta carotene desaturase or phytoene desaturase (or portions thereof) may be produced in heterologous host cells, particularly in the cells of microbial hosts, and can be used to prepare antibodies to the these proteins by methods well known to those skilled in the art. The antibodies are useful for detecting zeta carotene desaturase or phytoene desaturase in situ in cells or in vitro in cell extracts. Preferred heterologous host cells for production of the instant zeta carotene desaturase or phytoene desaturase are microbial hosts. Microbial expression systems and expression vectors containing regulatory sequences that direct high level expression of foreign proteins are well known to those skilled in the art. Any of these could be used to construct a chimeric gene for production of the instant zeta carotene desaturase or phytoene desaturase. This chimeric gene could then be introduced into appropriate microorganisms via transformation to provide high level expression of the encoded carotenoid biosynthetic enzyme. An example of a vector for high level expression of the instant zeta carotene desaturase or phytoene desaturase in a bacterial host is provided (Example 7).

Additionally, the instant zeta carotene desaturase or phytoene desaturase can be used as targets to facilitate design and/or identification of inhibitors of those enzymes that may be useful as herbicides. This is desirable because the zeta carotene desaturase and the phytoene desaturase described herein catalyze various steps in carotenoid biosynthesis. Accordingly, inhibition of the activity of either one or both of the enzymes described herein could lead to inhibition plant growth. Thus, the instant zeta carotene desaturase or phytoene desaturase could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the zeta carotene desaturase or the phytoene desaturase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a zeta carotene desaturase or a phytoene desaturase can be identified and obtained. This mutant plant can then be used to determine or confirm the natural function of the zeta carotene desaturase or the phytoene desaturase gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various rice, soybean and wheat tissues were prepared. The characteristics of the libraries are described below.

TABLE 2 cDNA Libraries from Rice, Soybean and Wheat

| Library | Tissue | Clone |
|---------|--------|-------|
| rls6 | Rice Leaf 15 Days After Germination, 6 Hours After Infection of Strain *Magaporthe grisea* 4360-R-67 (AVR2-YAMO); Susceptible | rlr6.pk0027.d5 rls6.pk0080.a9 |
| sr1 | Soybean Root | sr1.pk0022.a12 |
| wlm12 | Wheat Seedlings 12 Hours After Inoculation With *Erysiphe graminis f. sp tritici* | wlm12.pk0003.g5 |
| wlm24 | Wheat Seedlings 24 Hours After Inoculation With *Erysiphe graminis f. sp tritici* | wlm24.pk0031.e9 | cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding carotenoid biosynthetic enzymes were identified by conducting BLAST (Basic Local Alignment Search Tool; Altschul, S. F., et al., (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Zeta Carotene Desaturase

The BLASTX search using the EST sequences from clones csi1n.pk0010.f11, r1s6.pk0080.a9, r1r6.pk0074.h3, sr1.pk0022.a12, sr1.pk0023.e7, wlm24.pk003wre1n.pk0058.h12 revealed similarity of the proteins encoded by the cDNAs to Zeta Carotene Desaturase from Narcissus pseudonarcissus and Caspicum annum (GenBank Accession No. AJ224683 and 1583601, respectively). Further analysis of the sequences from clones rls6.pk0080.a9 and rlr6.pk0074.h3 revealed a significant region of overalp, thus affording the assembly of a contig encoding a portion of a rice Zeta Carotene Desaturase. Likewise, analysis of the sequences from clones sr1.pk0022.a12 and sr1.pk0023.e7 revealed a significant region of overalp, thus affording the assembly of a contig encoding a portion of a soybean Zeta Carotene Desaturase.

The BLAST results for each of these ESTs and contigs are shown in Table 3:

TABLE 3

BLAST Results for Clones Encoding Polypeptides Homologous to Zeta Carotene Desaturase

| Clone | Organism | GenBank Accession No. | BLAST pLog Score |
|---|---|---|---|
| csi1n.pk0010.f11 | Narcissus pseudonarcissus | AJ224683 | 50.30 |
| Contig formed of: rls6.pk0080.a9 rlr6.pk0074.h3 | Caspicum annum | 1583601 | 40.30 |
| Contig formed of sr1.pk0022.a12 sr1.pk0023.e7 | Caspicum annum | 1583601 | 10.10 |
| wlm24.pk0031.e9 | Narcissus pseudonarcissus | AJ224683 | 18.00 |
| wre1n.pk0058.h12 | Narcissus pseudonarcissus | AJ224683 | 50.70 |

The sequence of the entire cDNA insert in clone csi1n.pk0010.f11 was determined. BLASTP analysis indicated that it is identical to zeta carotene desaturase from *Zea mays* (NCBI General Identifier No. 4105563). The 5'-terminal sequence of the cDNA insert in clone rls6.pk0080.a9 was determined and is shown in SEQ ID NO:1; this sequence includes the partial sequence from clone rlr6.pk0074.h3. The deduced amino acid sequence of this cDNA is shown in SEQ ID NO:2. The 3'-terminal sequence of the cDNA insert in clone rls6.pk0080.a9 was determined and is shown in SEQ ID NO:3; the deduced amino acid sequence of this cDNA is shown in SEQ ID NO:4. The sequence of the entire cDNA insert in clone sr1.pk0022.a12 was determined and is shown in SEQ ID NO:7; the deduced amino acid sequence of this cDNA is shown in SEQ ID NO:8. The amino acid sequence set forth in SEQ ID NO:8 was evaluated by BLASTP, yielding a pLog value of>254 versus the *Caspicum annum* sequence (NCBI General Identifier No. 2129927; SEQ ID NO:13). The sequence of the entire cDNA insert in clone wlm24.pk0031.e9 was determined and is shown in SEQ ID NO:7; the deduced amino acid sequence of this cDNA is shown in SEQ ID NO:8. The amino acid sequence set forth in SEQ ID NO:8 was evaluated by BLASTP, yielding a pLog value of>254 versus the *Zea mays* sequence (NCBI General Identifier No. 4105563; SEQ ID NO:14). The amino acid sequence set forth in SEQ ID NO:6 is 82.9% similar to the *Capsicum annuum* sequence and the amino acid sequence set forth in SEQ ID NO:8 is 86.4% similar to the *Zea mays* sequence.

Sequence alignments and percent similarity calculations were performed using the Megalign program of the LASARGENE bioinformatics computing suite (DNASTAR Inc., Madison, Wis.). Multiple alignment of the amino acid sequences was performed using the Clustal method of alignment (Higgins, D. G. and Sharp, P. M. (1989) *CABIOS*. 5:151–153) with the default parameters (GAP PENALTY= 10, GAP LENGTH PENALTY=10).

Sequence alignments and BLAST scores and probabilities indicate that the instant nucleic acid fragments encode portions of a rice zeta carotene desaturase and entiresoy bean and wheat zeta carotene desaturases. These sequences represent the first rice, soybean and wheat sequences encoding zeta carotene desaturase.

Example 4

Characterization of cDNA Clones Encoding Phytoene Desaturase

The BLASTX search using the EST sequences from clones rlr6.pk0027.d5 and wlm12.pk0003.g5 revealed similarity of the proteins encoded by the cDNAs to Phytoene Desaturase from Zea maize and Narcissus pseudonarcissus (GenBank Accession Nos. U37285 and X78815, respectively). The BLAST results for each of these ESTs are shown in Table 4:

TABLE 4

BLAST Results for Clones Encoding Polypeptides Homologous to Phytoene Desaturase

| Clone | Organism | GenBank Accession No. | BLAST pLog Score |
|---|---|---|---|
| rlr6.pk0027.d5 | Zea maize | U37285 | 20.15 |
| wlm12.pk0003.g5 | Narcissus pseudonarcissus | X78815 | 29.70 |

The sequence of the entire cDNA insert in clone rlr6.pk0027.d5 was determined and is shown in SEQ ID NO:9; the deduced amino acid sequence of this cDNA is shown in SEQ ID NO:10. The amino acid sequence set forth in SEQ ID NO:10 was evaluated by BLASTP, yielding a pLog value of >254 versus the Zea mays sequence (NCBI General Identifier No. 1345838; SEQ ID NO:15). The sequence of the entire cDNA insert in clone wlm 12.pk0003.g5 was determined and is shown in SEQ ID NO:11; the deduced amino acid sequence of this cDNA is shown in SEQ ID NO:12. The amino acid sequence set forth in SEQ ID NO:12 was evaluated by BLASTP, yielding a pLog value of>254 versus the Zea mays sequence sequence. The amino acid sequence set forth in SEQ ID NO:10 is 89.3% similar to the Zea mays sequence while the amino acid sequence set forth in SEQ ID NO:12 is 89.1% similar to the Zea mays sequence.

Sequence alignments and percent similarity calculations were performed using the Megalign program of the LASAR-GENE bioinformatics computing suite (DNASTAR Inc., Madison, Wis.). Multiple alignment of the amino acid sequences was performed using the Clustal method of alignment (Higgins, D. G. and Sharp, P. M. (1989) CABIOS. 5:151–153) with the default parameters (GAP PENALTY= 10, GAP LENGTH PENALTY=10).

Sequence alignments and BLAST scores and probabilities indicate that the instant nucleic acid fragments encode entire or nearly entire rice and wheat phytoene desaturases. These sequences represent the first rice and wheat sequences encoding phytoene desaturase.

Example 5

Expression of Chimeric Genes in Monocot Cells

A chimeric gene comprising a cDNA encoding a carotenoid biosynthetic enzyme in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Nco I or Sma I) can be incorporated into the oligonucleotides to provide proper orientation of the DNA fragment when inserted into the digested vector pML 103 as described below. Amplification is then performed in a standard PCR. The amplified DNA is then digested with restriction enzymes Nco I and SmaI and fractionated on an agarose gel. The appropriate band can be isolated from the gel and combined with a 4.9 kb Nco I-Sma I fragment of the plasmid pML103. Plasmid pML 103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb Sal I-Nco I promoter fragment of the maize 27 kD zein gene and a 0.96 kb Sma I-Sal I fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a carotenoid biosynthetic enzyme, and the 10 kD zein 3' region.

The chimeric gene described above can then be introduced into corn cells by the following procedure. Immature corn embryos can be dissected from developing caryopses derived from crosses of the inbred corn lines H99 and LH 132. The embryos are isolated 10 to 11 days after pollination when they are 1.0 to 1.5 mm long. The embryos are then placed with the axis-side facing down and in contact with agarose-solidified N6 medium (Chu et al., (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein T. M. et al., (1987) Nature 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 µg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 6

Expression of Chimeric Genes in Dicot Cells

A seed-specific expression cassette composed of the promoter and transcription terminator from the gene encoding the i subunit of the seed storage protein phaseolin from the bean *Phaseolus vulgaris* (Doyle et al. (1986) *J Biol. Chem.* 261:9228–9238) can be used for expression of the instant carotenoid biosynthetic enzyme in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embroys may then be transformed with the expression vector comprising sequences encoding a carotenoid biosynthetic enzyme. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein T. M. et al. (1987) *Nature* (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the carotenoid biosynthetic enzyme and the phaseolin 3' region can be isolated as a restriction fragment. This fragment can then be inserted into a unique restriction site of the vector carrying the marker gene. To 50 $\mu$L of a 60 mg/mL 1 $\mu$m gold particle suspension is added (in order): 5 $\mu$L DNA (1 $\mu$g/$\mu$L), 20 $\mu$l spermidine (0.1 M), and 50 $\mu$L $CaCl_2$ (2.5 M). The particle preparation is then agitated for three minutes, spun in a microfuge for 10 seconds and the supernatant removed. The DNA-coated particles are then washed once in 400 $\mu$L 70% ethanol and resuspended in 40 $\mu$L of anhydrous ethanol. The DNA/particle suspension can be sonicated three times for one second each. Five $\mu$L of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant carotenoid biosynthetic enzyme can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the carotenoid biosynthetic enzyme are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Carotenoid Biosynthetic Enzymes The carotenoid biosynthetic enzymes described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant carotenoid biosynthetic enzymes may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant carotenoid biosynthetic enzymes, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the carotenoid biosynthetic enzymes are expressed as fusion proteins, the purification protocol may include the use of an affinity resin which is specific for the fusion protein tag attached to the expressed enzyme or an affinity resin containing ligands which are specific for the enzyme. For example, a carotenoid biosynthetic enzyme may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the carotenoid biosynthetic enzymes disclosed herein. Assays may be conducted under well known experimental conditions which permit optimal enzymatic activity. For example, assays for zeta carotene desaturase are presented by Linden H. et al. (1994) *Plant Mol. Biol.* 24:369–379. Assays for phytoene desaturase are presented by Pecker I. et al. (1992) *Proc Natl Acad Sci USA* 89:4962–4966.

What is claimed is:

1. An isolated polynucleotide comprising:
   (a) a nucleotide sequence encoding a polypeptide having phytoene desaturase activity, wherein the amino acid sequence of the polypeptide and the amino acid sequence of SEQ ID NO:10 have at least 95% sequence identity based on the Clustal alignment method, or
   (b) the complement of the nucleotide sequence, wherein the complement and the nucleotide sequence contain the same number of nucleotides and are 100% complementary.

2. The polynucleotide of claim 1 wherein the polypeptide comprises the amino acid sequence of SEQ ID NO:10.

3. The polynucleotide of claim 1 wherein the nucleotide sequence comprises the nucleotide sequence of SEQ ID NO:9.

4. A vector comprising the polynucleotide of claim 1.

5. A recombinant DNA construct comprising the polynucleotide of claim 1 operably linked to a regulatory sequence.

6. A method for transforming a cell comprising transforming a cell with the polynucleotide of claim 1.

7. A cell comprising the recombinant DNA construct of claim 5.

8. A method for producing a plant comprising transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

* * * * *

UNITED STATES PATENT AND TRADEMARK OFFICE
CERTIFICATE OF CORRECTION

PATENT NO. : 6,600,089 B1 Page 1 of 1
DATED : July 29, 2003
INVENTOR(S) : Cahoon Rebecca E. and Weng Zude It is certified that error appears in the above-identified patent and that said Letters Patent is hereby corrected as shown below:

<u>Title page,</u>
Item [75], Inventors, please delete "Anthony J. Kinney, Wilmington, DE (US); Steven J. Vollmer, Wilmington, DE (US);".

Signed and Sealed this

Tenth Day of August, 2004

JON W. DUDAS
*Acting Director of the United States Patent and Trademark Office*

SEQUENCE LISTING

<160> NUMBER OF SEQ ID NOS: 15

<210> SEQ ID NO 1
<211> LENGTH: 552
<212> TYPE: DNA
<213> ORGANISM: Oryza sativa

<400> SEQUENCE: 1

| | | | | | |
|---|---|---|---|---|---|
| gcacgaggtt | ctaaccagtg | gtgcgcgcgt | ggtggcgcca | cggaggccga | caaatccgct | 60 |
| gctcgacggc | atcttcgcct | cctcccccac | ccgcatcctc | ttccacctct | cgcgctcacg | 120 |
| ccatttatac | tctcctcctc | ctcctcctcc | tctactccta | gcagcagcgt | tggttggtga | 180 |
| gctgaggcat | atggccatgg | ctgccacgtc | ccgcgcgccg | tccacgctgg | ccccggcgtc | 240 |
| gttctccgcc | gccggcggca | gcaggaggcg | cgccggtgc | ccgaatccca | gggtgcgggt | 300 |
| gggggtgggg | gtgcggtgct | cgctcgacag | caacgtctcc | gacatggccg | tcaacgctcc | 360 |
| gaaaggattg | ttcccgccgg | agccggagca | ctacagggg | ccgaagctga | aggtggccat | 420 |
| catatgggcc | gggctcgccg | gcatgtccac | cgcggtggag | ctcttggacc | agtgccatga | 480 |
| ggttgatctg | tacgagtccc | ggccgtttat | cggtgggaaa | gtcggttctt | tgtggatac | 540 |
| gaaaggcaac | ag | | | | | 552 |

<210> SEQ ID NO 2
<211> LENGTH: 120
<212> TYPE: PRT
<213> ORGANISM: Oryza sativa

<400> SEQUENCE: 2

Met Ala Met Ala Ala Thr Ser Arg Ala Pro Ser Thr Leu Ala Pro Ala
 1               5                  10                  15
Ser Phe Ser Ala Ala Gly Gly Ser Arg Arg Arg Arg Cys Pro Asn
            20                  25                  30
Pro Arg Val Arg Val Gly Val Gly Val Arg Cys Ser Leu Asp Ser Asn
        35                  40                  45
Val Ser Asp Met Ala Val Asn Ala Pro Lys Gly Leu Phe Pro Pro Glu
    50                  55                  60
Pro Glu His Tyr Arg Gly Pro Lys Leu Lys Val Ala Ile Ile Trp Ala
65                  70                  75                  80
Gly Leu Ala Gly Met Ser Thr Ala Val Glu Leu Leu Asp Gln Cys His
                85                  90                  95
Glu Val Asp Leu Tyr Glu Ser Arg Pro Phe Ile Gly Gly Lys Val Gly
            100                 105                 110
Ser Phe Val Asp Thr Lys Gly Asn
        115                 120

<210> SEQ ID NO 3
<211> LENGTH: 844
<212> TYPE: DNA
<213> ORGANISM: Oryza sativa

<400> SEQUENCE: 3

| | | | | | |
|---|---|---|---|---|---|
| tttttttttt | tttttttttt | tttttttttt | tttttttttt | tttttttttt | tttttttttt | 60 |
| tttttttttt | tttttaagca | ccatctctca | caagatttta | agtgatgtgt | gcactatata | 120 |
| aacatcatca | tcatcatcaa | tgggttcaat | gatcggttaa | gctgaacaaa | acacacgctg | 180 |
| cctgatgtaa | tcccgtatgc | cacctttggt | tcccaatcac | aaattcacaa | taacgaagaa | 240 |

-continued

```
cacaccattg acgggcgaac gaacgatcgt gtcaaggcaa aaagggcagc agcagattgg      300
acctaaatgc tcaatcaagt aggatttaca tgagagtcgc tgcggaaatc gcctactaca      360
cccaggaagc tgttttttgtt ttgggcatag caatccactc actccagcat gtgtcatttg     420
aggaagctca gcttgtctga agggcctcga ccttacccct ggccttttcg ctgtcgtcga      480
caatgagctt ctttcggagg gcgagcagct cctctcctgc accacagatg taggccgcgg      540
ttctcctgcc tgagagagtt gccccttcca tgctgtcaat gtagtcctgt tttgtgtaag      600
agccagacag gaagaagttt ttaactggtg tcttttgatc aggtctaaat ggattaattc      660
ctggggactc gcggtacaat gattgaccga ttttcaccaa actcgaccaa gttagttcca      720
agccctggga tgacgggaac aattcttaga cctggttttg gaccctggca ataaccccct      780
caatccggaa tgggaagtta aggatgccaa gggttaacac aacttggatt aaagaacctt      840
gccc                                                                   844
```

<210> SEQ ID NO 4
<211> LENGTH: 138
<212> TYPE: PRT
<213> ORGANISM: Oryza sativa
<220> FEATURE:
<221> NAME/KEY: UNSURE
<222> LOCATION: (33)
<223> OTHER INFORMATION: Xaa = any amino acid

<400> SEQUENCE: 4

```
Gly Gln Gly Ser Leu Ile Gln Val Val Leu Thr Leu Gly Ile Leu Asn
 1               5                  10                  15

Phe Pro Phe Arg Ile Glu Gly Leu Phe Ala Arg Val Gln Asn Gln Val
            20                  25                  30

Xaa Glu Leu Phe Pro Ser Ser Gln Gly Leu Glu Leu Thr Trp Ser Ser
        35                  40                  45

Leu Val Lys Ile Gly Gln Ser Leu Tyr Arg Glu Ser Pro Gly Ile Asn
    50                  55                  60

Pro Phe Arg Pro Asp Gln Lys Thr Pro Val Lys Asn Phe Phe Leu Ser
65                  70                  75                  80

Gly Ser Tyr Thr Lys Gln Asp Tyr Ile Asp Ser Met Glu Gly Ala Thr
                85                  90                  95

Leu Ser Gly Arg Arg Thr Ala Ala Tyr Ile Cys Gly Ala Gly Glu Glu
            100                 105                 110

Leu Leu Ala Leu Arg Lys Lys Leu Ile Val Asp Asp Ser Glu Lys Ala
        115                 120                 125

Arg Gly Lys Val Glu Ala Leu Gln Thr Ser
    130                 135
```

<210> SEQ ID NO 5
<211> LENGTH: 1867
<212> TYPE: DNA
<213> ORGANISM: Glycine max

<400> SEQUENCE: 5

```
gcacgagctt tcaccttcac ctatggccat ggcttctttg attcagtgtt ctgcaacttc       60
cctctccgct gtcccatca ctacccgttt caccaggacc cacaagtctc gccttcgctg      120
ctccttagat gctaatgttt ccgacatgag cgttaacgcg ccaaaagggt tgtttcctcc     180
ggaacctgaa cattatcgag gaccaaaact gaaagtggca attattggag ctggacttgc     240
aggcatgtca actgcagtgg aactcttgga tcaaggccat gaggtggata tctatgagtc     300
```

-continued

```
aagacctttt attggtggca aagttggctc ttttgttgac aaaggtggga atcacattga    360
aatgggattg catgttttct ttggttgcta caacaatctt ttccgattgt tgaagaaggt    420
gggtgcagaa acaatctac ttgtgaagga tcacactcac acttttgtta acaaaggggg    480
tcaaattggt gaactggatt ttcgcttccc aattggggca ccaatacacg ggataagggc    540
gtttttgacc acaaatcagc ttaatactta tgataaggct agaaatgctg tggctcttgc    600
actcagtcca gttgtcagag ctcttgttga tccagatggt gcactgaggg acataaggaa    660
tttggatagt attagctttt cagattggtt tttatccaaa ggtggcacac gcatgagtat    720
tacaaaaatg tgggatccag ttgcctatgc ccttgggttt atcgactgtg ataatatcag    780
tgctcgctgc atgctcacca tatttgcatt gtttgccaca aagaccgagg cttccctttt    840
gcgaatgctg aagggttcac cggatgttta tctgagtggc cccatccgaa agtacatcat    900
ggacagaggg gcaggttcc atcttaggtg gggatgcaga gaactgcttt atgacaaatc    960
tgctgatggg agtatttatg ttacaggact ttccatgtca aaggccactg ccaagaaaat   1020
tgtgaaagct gatgcttatg ttgctgcttg tgatgtccct ggaattaaga gattacttcc   1080
atcagagtgg agggaacagg agттттттcaa taatatctat gaactagttg gagttcctgt   1140
agtcacagtg caactcagat acaatggttg ggttacagag ttgcaggatc tagaaaagtc   1200
aaggcgactg gggaaagctg ttgggttgga taaccttctc tatacacccg atgcagattt   1260
ttcttgcttt gcagaccttg cactttcatc tccagaggat ташncaттg agggacaagg   1320
atcattgctc caatgtgttc tgacgccagg agatccatac atgcccttac caaatgacga   1380
aattattgca agggtagcaa acaggttttt ggcactgttc ccatcatctc aaggtttgga   1440
agtgacttgg tcttctgttg ttaaaattgg ccaatctctg taccgtgagg gtcctggtaa   1500
agatccatat agacctgatc aaaagacacc agtgaggaat ttctttcttg ctggctctta   1560
cacaaagcag gactacatag acagcatgga aggtgcaacc ttgtctggca gacaagcttc   1620
ggcctatatc tgcgatgcag gggaagaatt agtggcattg cggaagaagc tcgacgctga   1680
gtttaaagac gacttaaaaa tatcaaatac taaagatgaa ttgagcttag tatgataaat   1740
ttcatgagg tggtcatgtt gacatgaagc aatctggttt ttttgcatgc aacatttttc   1800
aatgtatatt caatcgataa ataattacag aatagattgt ttcgaagcaa aaaaaaaaaa   1860
aaaaaaa                                                            1867
```

<210> SEQ ID NO 6
<211> LENGTH: 568
<212> TYPE: PRT
<213> ORGANISM: Glycine max

<400> SEQUENCE: 6

```
Met Ala Ser Leu Ile Gln Cys Ser Ala Thr Ser Leu Ser Ala Val Pro
  1               5                  10                  15

Ile Thr Thr Arg Phe Thr Arg Thr His Lys Ser Arg Leu Arg Cys Ser
             20                  25                  30

Leu Asp Ala Asn Val Ser Asp Met Ser Val Asn Ala Pro Lys Gly Leu
         35                  40                  45

Phe Pro Pro Glu Pro Glu His Tyr Arg Gly Pro Lys Leu Lys Val Ala
     50                  55                  60

Ile Ile Gly Ala Gly Leu Ala Gly Met Ser Thr Ala Val Glu Leu Leu
 65                  70                  75                  80

Asp Gln Gly His Glu Val Asp Ile Tyr Glu Ser Arg Pro Phe Ile Gly
```

-continued

```
                        85                      90                        95
Gly Lys Val Gly Ser Phe Val Asp Lys Gly Gly Asn His Ile Glu Met
                100                 105                 110
Gly Leu His Val Phe Phe Gly Cys Tyr Asn Asn Leu Phe Arg Leu Leu
            115                 120                 125
Lys Lys Val Gly Ala Glu Asn Asn Leu Leu Val Lys Asp His Thr His
        130                 135                 140
Thr Phe Val Asn Lys Gly Gly Gln Ile Gly Glu Leu Asp Phe Arg Phe
145                 150                 155                 160
Pro Ile Gly Ala Pro Ile His Gly Ile Arg Ala Phe Leu Thr Thr Asn
                165                 170                 175
Gln Leu Asn Thr Tyr Asp Lys Ala Arg Asn Ala Val Ala Leu Ala Leu
                180                 185                 190
Ser Pro Val Val Arg Ala Leu Val Asp Pro Asp Gly Ala Leu Arg Asp
            195                 200                 205
Ile Arg Asn Leu Asp Ser Ile Ser Phe Ser Asp Trp Phe Leu Ser Lys
        210                 215                 220
Gly Gly Thr Arg Met Ser Ile Thr Lys Met Trp Asp Pro Val Ala Tyr
225                 230                 235                 240
Ala Leu Gly Phe Ile Asp Cys Asp Asn Ile Ser Ala Arg Cys Met Leu
                245                 250                 255
Thr Ile Phe Ala Leu Phe Ala Thr Lys Thr Glu Ala Ser Leu Leu Arg
                260                 265                 270
Met Leu Lys Gly Ser Pro Asp Val Tyr Leu Ser Gly Pro Ile Arg Lys
            275                 280                 285
Tyr Ile Met Asp Arg Gly Gly Arg Phe His Leu Arg Trp Gly Cys Arg
        290                 295                 300
Glu Leu Leu Tyr Asp Lys Ser Ala Asp Gly Ser Ile Tyr Val Thr Gly
305                 310                 315                 320
Leu Ser Met Ser Lys Ala Thr Ala Lys Lys Ile Val Lys Ala Asp Ala
                325                 330                 335
Tyr Val Ala Ala Cys Asp Val Pro Gly Ile Lys Arg Leu Leu Pro Ser
                340                 345                 350
Glu Trp Arg Glu Gln Glu Phe Phe Asn Asn Ile Tyr Glu Leu Val Gly
            355                 360                 365
Val Pro Val Val Thr Val Gln Leu Arg Tyr Asn Gly Trp Val Thr Glu
        370                 375                 380
Leu Gln Asp Leu Glu Lys Ser Arg Arg Leu Gly Lys Ala Val Gly Leu
385                 390                 395                 400
Asp Asn Leu Leu Tyr Thr Pro Asp Ala Asp Phe Ser Cys Phe Ala Asp
                405                 410                 415
Leu Ala Leu Ser Ser Pro Glu Asp Tyr Tyr Ile Glu Gly Gln Gly Ser
                420                 425                 430
Leu Leu Gln Cys Val Leu Thr Pro Gly Asp Pro Tyr Met Pro Leu Pro
            435                 440                 445
Asn Asp Glu Ile Ile Ala Arg Val Ala Lys Gln Val Leu Ala Leu Phe
        450                 455                 460
Pro Ser Ser Gln Gly Leu Glu Val Thr Trp Ser Ser Val Val Lys Ile
465                 470                 475                 480
Gly Gln Ser Leu Tyr Arg Glu Gly Pro Gly Lys Asp Pro Tyr Arg Pro
                485                 490                 495
Asp Gln Lys Thr Pro Val Arg Asn Phe Phe Leu Ala Gly Ser Tyr Thr
                500                 505                 510
```

Lys Gln Asp Tyr Ile Asp Ser Met Glu Gly Ala Thr Leu Ser Gly Arg
            515                 520                 525

Gln Ala Ser Ala Tyr Ile Cys Asp Ala Gly Glu Glu Leu Val Ala Leu
        530                 535                 540

Arg Lys Lys Leu Asp Ala Glu Phe Lys Asp Leu Lys Ile Ser Asn
545                 550                 555                 560

Thr Lys Asp Glu Leu Ser Leu Val
                565

<210> SEQ ID NO 7
<211> LENGTH: 2074
<212> TYPE: DNA
<213> ORGANISM: Triticum aestivum

<400> SEQUENCE: 7

| | | | | | |
|---|---|---|---|---|---|
| cgctcacaca | atttatgcta | ttcctcgccc | agtggctcca | tcttccggc | tccgtccctc | 60 |
| actgctcctc | gggttttgta | ctgcttttgc | atcgacgagg | ccacggccat | ggccgccacg | 120 |
| tcgtgcgcgc | tagtctcggc | cctcgtagtc | ggccggcgcc | gcgggccgtc | ctgccagcgc | 180 |
| gcggcggccg | ccggtgtggt | tcgatgctcg | ctcgacagca | aggtctccga | catggccatc | 240 |
| aacgcaccga | aaggactgtt | cccgccggag | cctgagcact | acaggggccc | gaagctcaag | 300 |
| gtcgccatca | taggtgccgg | cctcgccggc | atgtccaccg | cagtagagct | cttggaccag | 360 |
| ggacatgagg | ttgatctgta | tgactcccga | acttttattg | gcggcaaggt | tggttctttt | 420 |
| gtcgacaagc | atgggaacca | tatcgagatg | gggctgcatg | tcttctttgg | ttgttacagc | 480 |
| aatcttttcc | gcctcatgaa | gaaggttggg | gctgataata | atctactagt | caaggaacat | 540 |
| acccatactt | ttgtaaataa | aggggcatt | gttggtgaac | ttgattttcg | gttccctgtg | 600 |
| ggagctccat | tacatggtat | ccaagcattt | ctaagaacca | atcaactcaa | ggtttatgat | 660 |
| aaggcaagga | atgcagttgc | tctcgcccta | agcccagttg | ttcgagctct | tcttgatcca | 720 |
| gacggtgcat | tgcaacaagt | acgggacttg | gatgatgtaa | gtttcactga | ttggttcatg | 780 |
| tctagaggtg | gtactcgaga | gagcatcaca | agaatgtggg | atcctgttgc | ttatgctctt | 840 |
| ggttttatcg | actgtgataa | tatcagtgct | cgatgcatgc | ttactatttt | caccctgttt | 900 |
| gccacaaaga | cagaggcatc | tttgttgcgc | atgctaaagg | gctcacctga | tgtttactta | 960 |
| agtggcccaa | taaagaagta | cataacagac | aggggtggta | ggtttcactt | gaagtgggga | 1020 |
| tgccgagagg | ttctctacga | taagtcaccc | gatggagaga | cctatgtgaa | aggctttctc | 1080 |
| atctctaagg | ctacaagtag | tgagataatc | aaagcagatg | catatgttgc | agcttgtgat | 1140 |
| gtcccaggga | tcaaaagact | attaccatcg | gaatggaggg | aatgggatat | gtttgacaat | 1200 |
| atatacaagt | tagatggtgt | tcctgtagtc | actgttcagc | ttcgctacaa | tggatgggtt | 1260 |
| actgaagtcc | aagacttgga | gaaatcaaga | caactccaaa | aagcagttgg | cttgataat | 1320 |
| ctactctata | ctccagatgc | agacttctcc | tgttttttcag | accttgcact | gtcatctcct | 1380 |
| gctgactact | acattgaagg | acaaggttcc | ctgatccaag | ctgtgctaac | tccaggtgat | 1440 |
| ccgtacatgc | cattgccaaa | tgaggagatt | attagcaagg | ttgaaaaaca | ggtcttagat | 1500 |
| ttgtttccat | cagcccgagg | cttggaagtt | acatggtcca | gtgtggtaaa | gatcggacaa | 1560 |
| tccttgtacc | gtgaggctcc | tggaaatgat | ccatttagac | ctgaccagaa | gacaccagtt | 1620 |
| aaaaatttct | tcttgtctgg | ctcttacacg | aaacaggact | acattgacag | catggaagga | 1680 |
| gcaactcttt | ctggcaggcg | aacagcagcc | tacatctgtg | gtgctggaga | ggagttatta | 1740 |

-continued

```
gccattcgaa agaagctcat tgtcgatcac agcgagaagg cctccgggat ggttcaaatg    1800
ttgcaaacaa gttaaacctt gcaatcacca aagccagaat gccaaactat aggtttcagg    1860
gttataggcg attgtcaaca gtgatttcta taaatcttgt ttgcgcatta gatttggtgc    1920 tgccttttt ttagccgtga cacatttgca catcgcatgt tcctatctta caattggcaa     1980
ccaggtgtct aagtggcata taggaatata tcaggcagcg tgtatgttca gttaaacctt    2040
agcccgtcat tcgaatgatt gatgtcatat tgca                                2074
```

<210> SEQ ID NO 8
<211> LENGTH: 568
<212> TYPE: PRT
<213> ORGANISM: Triticum aestivum

<400> SEQUENCE: 8

```
Met Ala Ala Thr Ser Cys Ala Leu Val Ser Ala Leu Val Val Gly Arg
  1               5                  10                  15

Arg Arg Gly Pro Ser Cys Gln Arg Ala Ala Ala Gly Val Val Arg
             20                  25                  30

Cys Ser Leu Asp Ser Lys Val Ser Asp Met Ala Ile Asn Ala Pro Lys
         35                  40                  45

Gly Leu Phe Pro Pro Glu Pro Glu His Tyr Arg Gly Pro Lys Leu Lys
     50                  55                  60

Val Ala Ile Ile Gly Ala Gly Leu Ala Gly Met Ser Thr Ala Val Glu
 65                  70                  75                  80

Leu Leu Asp Gln Gly His Glu Val Asp Leu Tyr Asp Ser Arg Thr Phe
                 85                  90                  95

Ile Gly Gly Lys Val Gly Ser Phe Val Asp Lys His Gly Asn His Ile
            100                 105                 110

Glu Met Gly Leu His Val Phe Phe Gly Cys Tyr Ser Asn Leu Phe Arg
        115                 120                 125

Leu Met Lys Lys Val Gly Ala Asp Asn Asn Leu Leu Val Lys Glu His
    130                 135                 140

Thr His Thr Phe Val Asn Lys Gly Gly Ile Val Gly Glu Leu Asp Phe
145                 150                 155                 160

Arg Phe Pro Val Gly Ala Pro Leu His Gly Ile Gln Ala Phe Leu Arg
                165                 170                 175

Thr Asn Gln Leu Lys Val Tyr Asp Lys Ala Arg Asn Ala Val Ala Leu
            180                 185                 190

Ala Leu Ser Pro Val Val Arg Ala Leu Leu Asp Pro Asp Gly Ala Leu
        195                 200                 205

Gln Gln Val Arg Asp Leu Asp Asp Val Ser Phe Thr Asp Trp Phe Met
    210                 215                 220

Ser Arg Gly Gly Thr Arg Glu Ser Ile Thr Arg Met Trp Asp Pro Val
225                 230                 235                 240

Ala Tyr Ala Leu Gly Phe Ile Asp Cys Asp Asn Ile Ser Ala Arg Cys
                245                 250                 255

Met Leu Thr Ile Phe Thr Leu Phe Ala Thr Lys Thr Glu Ala Ser Leu
            260                 265                 270

Leu Arg Met Leu Lys Gly Ser Pro Asp Val Tyr Leu Ser Gly Pro Ile
        275                 280                 285

Lys Lys Tyr Ile Thr Asp Arg Gly Gly Arg Phe His Leu Lys Trp Gly
    290                 295                 300

Cys Arg Glu Val Leu Tyr Asp Lys Ser Pro Asp Gly Glu Thr Tyr Val
305                 310                 315                 320
```

Lys Gly Phe Leu Ile Ser Lys Ala Thr Ser Ser Glu Ile Ile Lys Ala
              325                 330                 335

Asp Ala Tyr Val Ala Ala Cys Asp Val Pro Gly Ile Lys Arg Leu Leu
              340                 345                 350

Pro Ser Glu Trp Arg Glu Trp Asp Met Phe Asp Asn Ile Tyr Lys Leu
              355                 360                 365

Asp Gly Val Pro Val Val Thr Val Gln Leu Arg Tyr Asn Gly Trp Val
          370                 375                 380

Thr Glu Val Gln Asp Leu Glu Lys Ser Arg Gln Leu Gln Lys Ala Val
385                 390                 395                 400

Gly Leu Asp Asn Leu Leu Tyr Thr Pro Asp Ala Asp Phe Ser Cys Phe
              405                 410                 415

Ser Asp Leu Ala Leu Ser Ser Pro Ala Asp Tyr Tyr Ile Glu Gly Gln
              420                 425                 430

Gly Ser Leu Ile Gln Ala Val Leu Thr Pro Gly Asp Pro Tyr Met Pro
              435                 440                 445

Leu Pro Asn Glu Glu Ile Ile Ser Lys Val Lys Gln Val Leu Asp
              450                 455                 460

Leu Phe Pro Ser Ala Arg Gly Leu Glu Val Thr Trp Ser Ser Val Val
465                 470                 475                 480

Lys Ile Gly Gln Ser Leu Tyr Arg Glu Ala Pro Gly Asn Asp Pro Phe
              485                 490                 495

Arg Pro Asp Gln Lys Thr Pro Val Lys Asn Phe Phe Leu Ser Gly Ser
              500                 505                 510

Tyr Thr Lys Gln Asp Tyr Ile Asp Ser Met Glu Gly Ala Thr Leu Ser
              515                 520                 525

Gly Arg Arg Thr Ala Ala Tyr Ile Cys Gly Ala Gly Glu Glu Leu Leu
              530                 535                 540

Ala Ile Arg Lys Lys Leu Ile Val Asp His Ser Glu Lys Ala Ser Gly
545                 550                 555                 560

Met Val Gln Met Leu Gln Thr Ser
              565

<210> SEQ ID NO 9
<211> LENGTH: 2430
<212> TYPE: DNA
<213> ORGANISM: Oryza sativa

<400> SEQUENCE: 9

```
gcacgaggtt taaccccct tgtcccttt cccaccgccc caaaaaccca cccctccct      60 gactcctccc cccgcagctt ccgccgtccg cctccgctcc cacgtcgccg cccgtcgtc    120 gtcgccgccg acgctcttgc gtgcttattt gtcaaatcag atctgaatat aattttagga  180
gttgcttcag catggatact ggctgccgt catctatgaa cataactgga accagccaag   240
caagatcttt tgcgggacaa cttcctactc ataggtgctt cgcaagtagc agcatccaag   300
cactgaaaag tagtcagcat gtgagctttg gagtgaaatc tcttgtctta aggaataaag   360 gaaaagatt ccgtcggagg ctcggtgctc tacaggttgt ttgccaggac tttccaagac   420
ctccactaga aaacacaata aacttttggg aagctggaca actatcttca tttttcagaa   480
acagtgaaca acccactaaa ccattacagg tcgtgattgc tggagcagga ttagctggtt   540
tatcaacggc aaaatatctg gcagatgctg gtcataaacc catattgctt gaggcaaggg   600
atgttttggg tggaaagata gctgcttgga aggatgaaga tggagattgg tatgaaactg   660
```

-continued

| | |
|---|---|
| ggcttcatat cttttttgga gcttatccca acatacagaa cttgtttggc gagcttggta | 720 |
| ttaatgatcg gttgcaatgg aaggaacact ccatgatatt tgccatgcca acaagccag | 780 |
| gagaattcag ccggtttgat tttcctgaaa cattgcctgc acccttaaat ggaatatggg | 840 |
| ccatactaag aaacaatgaa atgctaactt ggccagagaa ggtgaagttt gctcttggac | 900 |
| ttttgccagc aatggttggt ggccaagctt atgttgaagc tcaagatggt tttactgttt | 960 |
| ctgagtggat gaaaaagcag ggtgttcctg atcgagtgaa cgatgaggtt tcattgcaa | 1020 |
| tgtcaaaggc acttaatttc ataaatcctg atgagttatc catgcagtgc attctgattg | 1080 |
| ctttaaaccg atttcttcag gagaagcatg ttctaagat ggcattcttg atggtaatc | 1140 |
| ctcctgaaag gttatgcatg cctattgttg accatgttcg ctctttgggt ggtgaggttc | 1200 |
| ggctgaattc tcgtattcag aaaatagaac ttaatcctga tggaacagtg aaacactttg | 1260 |
| cacttactga tggaactcaa ataactggag atgcttatgt ttttgcaaca ccagttgata | 1320 |
| tcttgaagct tcttgtacct caagagtgga agaaatatc ttatttcaag aagctggaga | 1380 |
| agttggtggg agttcctgtt ataaatgttc atatatggtt tgatagaaaa ctgaagaaca | 1440 |
| catatgacca ccttcttttc agcaggagtt cacttttaag tgtttatgcg acatgtcag | 1500 |
| taacttgcaa ggaatactat gatcaaaaac gttcaatgct ggagttggtc tttgctcctg | 1560 |
| cagaggaatg ggttggacgg agtgacactg aaatcatcga agcaactatg caagagctag | 1620 |
| ccaagctatt tcctgatgaa attgctgctg atcagagtaa agcaaagatt ctgaagtatc | 1680 |
| atgttgtgaa gacaccaaga tctgtttaca agactatccc ggactgtgaa ccttgccgac | 1740 |
| ctctgcaaag atcaccgatt gaagggttct atctagctgg tgactacaca aagcagaaat | 1800 |
| atttggcttc gatggagggt gcagttctat ctgggaagct ttgtgctcag tctgtagtgg | 1860 |
| aggattataa aatgctatct cgtaggagcc tgaaaagtct gcagtctgaa gttcctgttg | 1920 |
| cctcctagtt gtagtcagga ctattcccaa tggtgtgtgt gtcatcatcc cctagtcagt | 1980 |
| tttttctat ttagtgggtg cccaactctc caccaattta cacatgatgg aacttgaaag | 2040 |
| atgcctattt tggtcttatc atatttctgt aaagttgatt tgtggtttaa acctcgtgcc | 2100 |
| gaattcggca cgaggtttaa acgtgagatc gtgacggttc ttccaaccga gctcgaggtt | 2160 |
| attcggccaa agaagagcga caagatcaag ataatgaacg gcaatttccg tggatactct | 2220 |
| ggaaagctca taggtataga tggttccgac ggcattgtga agcttgatga cacatacgaa | 2280 |
| gtcaagatct tagatatggt gattttggcc aaactggcga gttgagatgg atgtatattt | 2340 |
| tgtacgagtc catcgtatag ccaaatgttt gtaacagata ccctttgtag tcaataaaac | 2400 |
| gttttgttat ttaaaaaaaa aaaaaaaaaa | 2430 |

<210> SEQ ID NO 10
<211> LENGTH: 578
<212> TYPE: PRT
<213> ORGANISM: Oryza sativa

<400> SEQUENCE: 10

Met Asp Thr Gly Cys Leu Ser Ser Met Asn Ile Thr Gly Thr Ser Gln
 1               5                  10                  15

Ala Arg Ser Phe Ala Gly Gln Leu Pro Thr His Arg Cys Phe Ala Ser
            20                  25                  30

Ser Ser Ile Gln Ala Leu Lys Ser Ser Gln His Val Ser Phe Gly Val
        35                  40                  45

Lys Ser Leu Val Leu Arg Asn Lys Gly Lys Arg Phe Arg Arg Arg Leu

-continued

```
                50                    55                    60
        Gly Ala Leu Gln Val Val Cys Gln Asp Phe Pro Arg Pro Leu Glu
        65                    70                    75                    80
        Asn Thr Ile Asn Phe Leu Glu Ala Gly Gln Leu Ser Ser Phe Arg
                              85                    90                    95
        Asn Ser Glu Gln Pro Thr Lys Pro Leu Gln Val Val Ile Ala Gly Ala
                              100                   105                   110
        Gly Leu Ala Gly Leu Ser Thr Ala Lys Tyr Leu Ala Asp Ala Gly His
                              115                   120                   125
        Lys Pro Ile Leu Leu Glu Ala Arg Asp Val Leu Gly Gly Lys Ile Ala
                              130                   135                   140
        Ala Trp Lys Asp Glu Asp Gly Asp Trp Tyr Glu Thr Gly Leu His Ile
        145                   150                   155                   160
        Phe Phe Gly Ala Tyr Pro Asn Ile Gln Asn Leu Phe Gly Glu Leu Gly
                              165                   170                   175
        Ile Asn Asp Arg Leu Gln Trp Lys Glu His Ser Met Ile Phe Ala Met
                              180                   185                   190
        Pro Asn Lys Pro Gly Glu Phe Ser Arg Phe Asp Phe Pro Glu Thr Leu
                              195                   200                   205
        Pro Ala Pro Leu Asn Gly Ile Trp Ala Ile Leu Arg Asn Asn Glu Met
                              210                   215                   220
        Leu Thr Trp Pro Glu Lys Val Lys Phe Ala Leu Gly Leu Leu Pro Ala
        225                   230                   235                   240
        Met Val Gly Gly Gln Ala Tyr Val Glu Ala Gln Asp Gly Phe Thr Val
                              245                   250                   255
        Ser Glu Trp Met Lys Lys Gln Gly Val Pro Asp Arg Val Asn Asp Glu
                              260                   265                   270
        Val Phe Ile Ala Met Ser Lys Ala Leu Asn Phe Ile Asn Pro Asp Glu
                              275                   280                   285
        Leu Ser Met Gln Cys Ile Leu Ile Ala Leu Asn Arg Phe Leu Gln Glu
                              290                   295                   300
        Lys His Gly Ser Lys Met Ala Phe Leu Asp Gly Asn Pro Pro Glu Arg
        305                   310                   315                   320
        Leu Cys Met Pro Ile Val Asp His Val Arg Ser Leu Gly Gly Glu Val
                              325                   330                   335
        Arg Leu Asn Ser Arg Ile Gln Lys Ile Glu Leu Asn Pro Asp Gly Thr
                              340                   345                   350
        Val Lys His Phe Ala Leu Thr Asp Gly Thr Gln Ile Thr Gly Asp Ala
                              355                   360                   365
        Tyr Val Phe Ala Thr Pro Val Asp Ile Leu Lys Leu Leu Val Pro Gln
                              370                   375                   380
        Glu Trp Lys Glu Ile Ser Tyr Phe Lys Lys Leu Glu Lys Leu Val Gly
        385                   390                   395                   400
        Val Pro Val Ile Asn Val His Ile Trp Phe Asp Arg Lys Leu Lys Asn
                              405                   410                   415
        Thr Tyr Asp His Leu Leu Phe Ser Arg Ser Ser Leu Leu Ser Val Tyr
                              420                   425                   430
        Ala Asp Met Ser Val Thr Cys Lys Glu Tyr Tyr Asp Gln Lys Arg Ser
                              435                   440                   445
        Met Leu Glu Leu Val Phe Ala Pro Ala Glu Glu Trp Val Gly Arg Ser
                              450                   455                   460
        Asp Thr Glu Ile Ile Glu Ala Thr Met Gln Glu Leu Ala Lys Leu Phe
        465                   470                   475                   480
```

```
Pro Asp Glu Ile Ala Ala Asp Gln Ser Lys Ala Lys Ile Leu Lys Tyr
            485                 490                 495
His Val Lys Thr Pro Arg Ser Val Tyr Lys Thr Ile Pro Asp Cys
        500                 505                 510
Glu Pro Cys Arg Pro Leu Gln Arg Ser Pro Ile Glu Gly Phe Tyr Leu
            515                 520                 525
Ala Gly Asp Tyr Thr Lys Gln Lys Tyr Leu Ala Ser Met Glu Gly Ala
        530                 535                 540
Val Leu Ser Gly Lys Leu Cys Ala Gln Ser Val Val Glu Asp Tyr Lys
545                 550                 555                 560
Met Leu Ser Arg Arg Ser Leu Lys Ser Leu Gln Ser Glu Val Pro Val
                565                 570                 575
Ala Ser
```

<210> SEQ ID NO 11
<211> LENGTH: 1420
<212> TYPE: DNA
<213> ORGANISM: Triticum aestivum

<400> SEQUENCE: 11

```
gcacgaggtt tgctgagctt ggtattagtg atcgcttgca atggaaggaa cactccatga      60
tatttgccat gccaaacaaa ccaggagaat acagccgttt tgattttcca gagactttgc     120
cggcgccctt aaatggagtg tgggccatac tgaaaaacaa tgaaatgctt acttggccgg     180
agaaggtgaa gtttgctatt ggcttctac ctgcaatgct tggtggccaa gcttacgttg      240
aagctcaaga tggcttaact gtttcagaat ggatggaaaa gcagggtgtt cctgatcggg     300
tcaacgacga ggttttatt gcaatgtcca aggcactcaa tttcataaac cctgacgagt      360
tatccatgca gtgcattctg attgctctaa accgatttct ccaggagaag catggctcga     420
aaatggcatt cttggatggt aatcctcctg aaaggctatg catgcctatt gttaaccaca     480
ttcagtcttt gggtggtgag gtccggctga attctcgtat tcagaaaatt gaactgaacc     540
cggacggaac agtgaagcac tttgcactta ctgatgggac tcaaataact ggagatgcat     600
atgttttgc agcaccagtt gatatcttca agcttcttgt accacaagag tggagagaga     660
tctcttattt caaaaggctg gataagttgg tgggagttcc tgtcatcaat gttcatatat     720
ggtttgacag aaaactgaaa aacacgtatg accaccttct tttcagcagg agttcacttt     780
taagcgttta tgcagacatg tctttagcgt gcaaggagta ctatgatcca aaccgttcaa     840
tgctggagct ggtctttgct ccagcagagg aatggatcgg gcggagtgac accgaaatca     900
tcgaagcaac tatgctagag ctagccaagt tgtttcctga tgaaatcgct gctgaccaga     960
gtaaagcaaa gattcttaaa taccatgttg tgaagacacc gaggtccgtt tacaagactg    1020
tcccgaactg cgaaccttgc cgaccccctgc aacgatcacc gatcgaaggg ttctatctgg    1080
ccggcgatta cacaaagcag aaatacctgg cttccatgga gggtgcggtt tgtcaggga    1140
agttttgtgc tcagtccata gtgcaggatt ctaagatgct gtcccgcagg agccaggaga    1200
gcctgcaatc cgaagccccg gtcgcctcca agttgtagct agttagcgcg attcaaaatt    1260
ttttggcgt ttcctatatg tcattgtcac attgttgtag agtccaccag tgaattgagc     1320
tgacatccat attggaacta aaagggaaat ttgtaaaaca agaagacct tttgcagaag      1380
ggcaaaagtg ataaaaggaa tcttagatat caaaaaaaa                             1420
```

<210> SEQ ID NO 12

<211> LENGTH: 411
<212> TYPE: PRT
<213> ORGANISM: Triticum aestivum

<400> SEQUENCE: 12

```
Thr Arg Phe Ala Glu Leu Gly Ile Ser Asp Arg Leu Gln Trp Lys Glu
  1               5                  10                  15

His Ser Met Ile Phe Ala Met Pro Asn Lys Pro Gly Glu Tyr Ser Arg
             20                  25                  30

Phe Asp Phe Pro Glu Thr Leu Pro Ala Pro Leu Asn Gly Val Trp Ala
         35                  40                  45

Ile Leu Lys Asn Asn Glu Met Leu Thr Trp Pro Glu Lys Val Lys Phe
 50                  55                  60

Ala Ile Gly Leu Leu Pro Ala Met Leu Gly Gly Gln Ala Tyr Val Glu
 65                  70                  75                  80

Ala Gln Asp Gly Leu Thr Val Ser Glu Trp Met Glu Lys Gln Gly Val
             85                  90                  95

Pro Asp Arg Val Asn Asp Glu Val Phe Ile Ala Met Ser Lys Ala Leu
        100                 105                 110

Asn Phe Ile Asn Pro Asp Glu Leu Ser Met Gln Cys Ile Leu Ile Ala
        115                 120                 125

Leu Asn Arg Phe Leu Gln Glu Lys His Gly Ser Lys Met Ala Phe Leu
130                 135                 140

Asp Gly Asn Pro Pro Glu Arg Leu Cys Met Pro Ile Val Asn His Ile
145                 150                 155                 160

Gln Ser Leu Gly Gly Glu Val Arg Leu Asn Ser Arg Ile Gln Lys Ile
                165                 170                 175

Glu Leu Asn Pro Asp Gly Thr Val Lys His Phe Ala Leu Thr Asp Gly
            180                 185                 190

Thr Gln Ile Thr Gly Asp Ala Tyr Val Phe Ala Ala Pro Val Asp Ile
        195                 200                 205

Phe Lys Leu Leu Val Pro Gln Glu Trp Arg Glu Ile Ser Tyr Phe Lys
    210                 215                 220

Arg Leu Asp Lys Leu Val Gly Val Pro Val Ile Asn Val His Ile Trp
225                 230                 235                 240

Phe Asp Arg Lys Leu Lys Asn Thr Tyr Asp His Leu Leu Phe Ser Arg
                245                 250                 255

Ser Ser Leu Leu Ser Val Tyr Ala Asp Met Ser Leu Ala Cys Lys Glu
            260                 265                 270

Tyr Tyr Asp Pro Asn Arg Ser Met Leu Glu Leu Val Phe Ala Pro Ala
        275                 280                 285

Glu Glu Trp Ile Gly Arg Ser Asp Thr Glu Ile Ile Glu Ala Thr Met
    290                 295                 300

Leu Glu Leu Ala Lys Leu Phe Pro Asp Glu Ile Ala Ala Asp Gln Ser
305                 310                 315                 320

Lys Ala Lys Ile Leu Lys Tyr His Val Val Lys Thr Pro Arg Ser Val
                325                 330                 335

Tyr Lys Thr Val Pro Asn Cys Glu Pro Cys Arg Pro Leu Gln Arg Ser
            340                 345                 350

Pro Ile Glu Gly Phe Tyr Leu Ala Gly Asp Tyr Thr Lys Gln Lys Tyr
        355                 360                 365

Leu Ala Ser Met Glu Gly Ala Val Leu Ser Gly Lys Phe Cys Ala Gln
    370                 375                 380

Ser Ile Val Gln Asp Ser Lys Met Leu Ser Arg Arg Ser Gln Glu Ser
```

```
385                 390                 395                 400
Leu Gln Ser Glu Ala Pro Val Ala Ser Lys Leu
                405                 410

<210> SEQ ID NO 13
<211> LENGTH: 588
<212> TYPE: PRT
<213> ORGANISM: Capsicum annuum

<400> SEQUENCE: 13

Met Ala Thr Cys Ser Ala Tyr Leu Cys Cys Pro Ala Thr Ser Ala Ser
  1               5                  10                  15

Leu Lys Lys Arg Val Phe Pro Asp Gly Ser Ala Gly Phe Leu Phe Phe
                 20                  25                  30

Gly Gly Arg Arg Leu Ser Asn Arg Leu Val Thr Pro Lys Ser Val Ile
             35                  40                  45

Arg Ala Asp Leu Asn Ser Met Val Ser Asp Met Ser Thr Asn Ala Pro
         50                  55                  60

Lys Gly Leu Phe Pro Pro Glu Pro Glu His Tyr Arg Gly Pro Lys Leu
 65                  70                  75                  80

Lys Val Ala Ile Ile Gly Ala Gly Leu Ala Gly Met Ser Thr Ala Val
                 85                  90                  95

Glu Leu Leu Asp Gln Gly His Glu Val Asp Ile Tyr Glu Ser Arg Thr
                100                 105                 110

Phe Ile Gly Gly Lys Val Gly Ser Phe Val Asp Lys Arg Gly Asn His
            115                 120                 125

Ile Glu Met Gly Leu His Val Phe Phe Gly Cys Tyr Asn Asn Leu Phe
        130                 135                 140

Arg Leu Met Lys Lys Val Gly Ala Glu Lys Asn Leu Leu Val Lys Glu
145                 150                 155                 160

His Thr His Thr Phe Val Asn Lys Gly Gly Glu Ile Gly Glu Leu Asp
                165                 170                 175

Phe Arg Phe Pro Val Gly Ala Pro Leu His Gly Ile Asn Ala Phe Leu
            180                 185                 190

Ser Thr Asn Gln Leu Lys Thr Tyr Asp Lys Ala Arg Asn Ala Val Ala
        195                 200                 205

Leu Ala Leu Ser Pro Val Val Arg Ala Leu Val Asp Pro Asp Gly Ala
    210                 215                 220

Leu Gln Gln Ile Arg Asp Leu Asp Ser Val Ser Phe Ser Asp Trp Phe
225                 230                 235                 240

Met Ser Lys Gly Gly Thr Arg Ala Ser Ile Gln Arg Met Trp Asp Pro
                245                 250                 255

Val Ala Tyr Ala Leu Gly Phe Ile Asp Cys Asp Asn Ile Ser Ala Arg
            260                 265                 270

Cys Met Leu Thr Ile Phe Ala Leu Phe Ala Thr Lys Thr Glu Ala Ser
        275                 280                 285

Leu Leu Arg Met Leu Lys Gly Ser Pro Asp Val Tyr Leu Ser Gly Pro
    290                 295                 300

Ile Lys Lys Tyr Ile Ile Asp Lys Gly Gly Arg Phe His Leu Arg Trp
305                 310                 315                 320

Gly Cys Arg Glu Val Leu Tyr Glu Thr Ser Ser Asp Gly Ser Met Tyr
                325                 330                 335

Val Ser Gly Leu Ala Met Ser Lys Ala Thr Gln Lys Lys Ile Val Lys
            340                 345                 350
```

```
Ala Asp Ala Tyr Val Ala Ala Cys Val Val Pro Gly Ile Lys Arg Leu
            355                 360                 365

Val Pro Gln Lys Trp Arg Glu Leu Glu Phe Phe Gly Asn Ile Tyr Lys
        370                 375                 380

Leu Ile Gly Val Pro Val Val Thr Val Gln Leu Arg Tyr Asn Gly Trp
385                 390                 395                 400

Val Thr Glu Leu Gln Asp Leu Glu Arg Ser Arg Gln Ser Lys Arg Ala
                405                 410                 415

Thr Gly Leu Asp Asn Leu Leu Tyr Thr Pro Asp Ala Asp Phe Ser Cys
            420                 425                 430

Phe Ala Asp Leu Ala Leu Ala Ser Pro Glu Asp Tyr Tyr Ile Glu Gly
            435                 440                 445

Gln Gly Ser Leu Leu Gln Cys Val Leu Thr Pro Gly Asp Pro Tyr Met
        450                 455                 460

Pro Leu Pro Asn Glu Glu Ile Ile Arg Arg Val Ser Lys Gln Val Leu
465                 470                 475                 480

Ala Leu Phe Pro Ser Ser Gln Gly Leu Glu Val Thr Trp Ser Ser Val
                485                 490                 495

Val Lys Ile Gly Gln Ser Leu Tyr Arg Glu Gly Pro Gly Lys Asp Pro
            500                 505                 510

Phe Arg Pro Asp Gln Lys Thr Pro Val Glu Asn Phe Phe Leu Ala Gly
        515                 520                 525

Ser Tyr Thr Lys Gln Asp Tyr Ile Asp Ser Met Glu Gly Ala Thr Leu
530                 535                 540

Ser Gly Arg Gln Ala Ser Ala Tyr Ile Cys Asp Ala Gly Glu Gln Leu
545                 550                 555                 560

Leu Ala Leu Arg Lys Lys Ile Ala Ala Glu Leu Asn Glu Ile Ser
            565                 570                 575

Lys Gly Val Ser Leu Ser Asp Glu Leu Ser Leu Val
                580                 585

<210> SEQ ID NO 14
<211> LENGTH: 570
<212> TYPE: PRT
<213> ORGANISM: Zea mays

<400> SEQUENCE: 14

Met Ala Ser Val Ala Ala Thr Thr Leu Ala Pro Ala Leu Ala Pro
1               5                   10                  15

Arg Arg Ala Arg Pro Gly Thr Gly Leu Val Pro Pro Arg Arg Ala Ser
                20                  25                  30

Ala Val Ala Ala Arg Ser Thr Val Thr Ser Pro Thr Trp Arg Gln Arg
            35                  40                  45

Ser Gln Arg Leu Phe Pro Pro Glu Pro Glu His Tyr Arg Gly Pro Lys
        50                  55                  60

Leu Lys Val Ala Ile Ile Gly Ala Gly Leu Ala Gly Met Ser Thr Ala
65                  70                  75                  80

Val Glu Leu Leu Asp Gln Gly His Glu Val Asp Leu Tyr Glu Ser Arg
                85                  90                  95

Pro Phe Ile Gly Gly Lys Val Gly Ser Phe Val Asp Arg Gln Gly Asn
                100                 105                 110

His Ile Glu Met Gly Leu His Val Phe Phe Gly Cys Tyr Ser Asn Leu
            115                 120                 125

Phe Arg Leu Met Lys Lys Val Gly Ala Asp Asn Asn Leu Leu Val Lys
        130                 135                 140
```

-continued

```
Glu His Thr His Thr Phe Val Asn Lys Gly Thr Ile Gly Glu Leu
145                 150                 155                 160

Asp Phe Arg Phe Pro Val Gly Ala Pro Leu His Gly Ile Gln Ala Phe
            165                 170                 175

Leu Arg Thr Asn Gln Leu Lys Val Tyr Asp Lys Ala Arg Asn Ala Val
            180                 185                 190

Ala Leu Ala Leu Ser Pro Val Arg Ala Leu Val Asp Pro Asp Gly
            195                 200                 205

Ala Leu Gln Gln Val Arg Asp Leu Asp Ile Ser Phe Ser Asp Trp
210                 215                 220

Phe Met Ser Lys Gly Gly Thr Arg Glu Ser Ile Thr Arg Met Trp Asp
225                 230                 235                 240

Pro Val Arg Tyr Ala Leu Gly Phe Ile Asp Cys Asp Asn Ile Ser Ala
            245                 250                 255

Arg Cys Met Leu Thr Ile Phe Thr Leu Phe Ala Thr Lys Thr Glu Ala
            260                 265                 270

Ser Leu Leu Arg Met Leu Lys Gly Ser Pro Asp Val Tyr Leu Ser Gly
            275                 280                 285

Pro Ile Lys Lys Tyr Ile Thr Asp Arg Gly Arg Phe His Leu Arg
290                 295                 300

Trp Gly Cys Arg Glu Val Leu Tyr Glu Lys Ser Pro Asp Gly Glu Thr
305                 310                 315                 320

Tyr Val Lys Gly Leu Leu Leu Thr Lys Ala Thr Ser Arg Glu Ile Ile
            325                 330                 335

Lys Ala Asp Ala Tyr Val Ala Ala Cys Asp Val Pro Gly Ile Lys Arg
            340                 345                 350

Leu Leu Pro Ser Glu Trp Arg Glu Trp Glu Met Phe Asp Asn Ile Tyr
            355                 360                 365

Lys Leu Asp Gly Val Pro Val Val Thr Val Gln Leu Arg Tyr Asn Gly
            370                 375                 380

Trp Val Thr Glu Leu Gln Asp Leu Glu Lys Ser Arg Gln Leu Gln Arg
385                 390                 395                 400

Ala Val Gly Leu Asp Asn Leu Leu Tyr Thr Ala Asp Ala Asp Phe Ser
            405                 410                 415

Cys Phe Ser Asp Leu Ala Leu Ser Ser Pro Ala Asp Tyr Tyr Ile Glu
            420                 425                 430

Gly Gln Gly Ser Leu Ile Gln Ala Val Leu Thr Pro Gly Asp Pro Tyr
            435                 440                 445

Met Pro Leu Pro Asn Glu Glu Ile Ile Ser Lys Val Gln Lys Gln Val
450                 455                 460

Val Glu Leu Phe Pro Ser Ser Arg Gly Leu Glu Val Thr Trp Ser Ser
465                 470                 475                 480

Val Val Lys Ile Gly Gln Ser Leu Tyr Arg Glu Ala Pro Gly Asn Asp
            485                 490                 495

Pro Phe Arg Pro Asp Gln Lys Thr Pro Val Lys Asn Phe Phe Leu Ser
            500                 505                 510

Gly Ser Tyr Thr Lys Gln Asp Tyr Ile Asp Ser Met Glu Gly Ala Thr
            515                 520                 525

Leu Ser Gly Arg Arg Thr Ser Ala Tyr Ile Cys Gly Ala Gly Glu Glu
            530                 535                 540

Leu Leu Ala Leu Arg Lys Lys Leu Leu Ile Asp Asp Gly Glu Lys Ala
545                 550                 555                 560
```

-continued

Leu Gly Asn Val Gln Val Leu Gln Ala Ser
            565                 570

<210> SEQ ID NO 15
<211> LENGTH: 571
<212> TYPE: PRT
<213> ORGANISM: Zea mays

<400> SEQUENCE: 15

Met Asp Thr Gly Cys Leu Ser Ser Met Asn Ile Thr Gly Ala Ser Gln
  1               5                  10                  15

Thr Arg Ser Phe Ala Gly Gln Leu Pro Pro Gln Arg Cys Phe Ala Ser
                 20                  25                  30

Ser His Tyr Thr Ser Phe Ala Val Lys Lys Leu Val Ser Arg Asn Lys
             35                  40                  45

Gly Arg Arg Ser His Arg Arg His Pro Ala Leu Gln Val Val Cys Lys
         50                  55                  60

Asp Phe Pro Arg Pro Leu Glu Ser Thr Ile Asn Tyr Leu Glu Ala
 65                  70                  75                  80

Gly Gln Leu Ser Ser Phe Phe Arg Asn Ser Glu Arg Pro Ser Lys Pro
                 85                  90                  95

Leu Gln Val Val Val Ala Gly Ala Gly Leu Ala Gly Leu Ser Thr Ala
                100                 105                 110

Lys Tyr Leu Ala Asp Ala Gly His Lys Pro Ile Leu Leu Glu Ala Arg
            115                 120                 125

Asp Val Leu Gly Gly Lys Val Ala Ala Trp Lys Asp Glu Asp Gly Asp
        130                 135                 140

Trp Tyr Glu Thr Gly Leu His Ile Phe Phe Gly Ala Tyr Pro Asn Ile
145                 150                 155                 160

Gln Asn Leu Phe Gly Glu Leu Arg Ile Glu Asp Arg Leu Gln Trp Lys
                165                 170                 175

Glu His Ser Met Ile Phe Ala Met Pro Asn Lys Pro Gly Glu Phe Ser
            180                 185                 190

Arg Phe Asp Phe Pro Glu Thr Leu Pro Ala Pro Ile Asn Gly Ile Trp
        195                 200                 205

Ala Ile Leu Arg Asn Asn Glu Met Leu Thr Trp Pro Glu Lys Val Lys
    210                 215                 220

Phe Ala Ile Gly Leu Leu Pro Ala Met Val Gly Gly Gln Pro Tyr Val
225                 230                 235                 240

Glu Ala Gln Asp Gly Leu Thr Val Ser Glu Trp Met Lys Lys Gln Gly
                245                 250                 255

Val Pro Asp Arg Val Asn Asp Glu Val Phe Ile Ala Met Ser Lys Ala
            260                 265                 270

Leu Asn Phe Ile Asn Pro Asp Glu Leu Ser Met Gln Cys Ile Leu Ile
        275                 280                 285

Ala Leu Asn Arg Phe Leu Gln Glu Lys His Gly Ser Lys Met Ala Phe
    290                 295                 300

Leu Asp Gly Asn Pro Pro Glu Arg Leu Cys Met Pro Ile Val Asp His
305                 310                 315                 320

Ile Arg Ser Arg Gly Gly Glu Val Arg Leu Asn Ser Arg Ile Lys Lys
                325                 330                 335

Ile Glu Leu Asn Pro Asp Gly Thr Val Lys His Phe Ala Leu Ser Asp
            340                 345                 350

Gly Thr Gln Ile Thr Gly Asp Ala Tyr Val Cys Ala Thr Pro Val Asp
        355                 360                 365

```
Ile Phe Lys Leu Leu Val Pro Gln Glu Trp Ser Glu Ile Thr Tyr Phe
    370                 375                 380
Lys Lys Leu Glu Lys Leu Val Gly Val Pro Val Ile Asn Val His Ile
385             390                 395                     400
Trp Phe Asp Arg Lys Leu Asn Asn Thr Tyr Asp His Leu Leu Phe Ser
            405                 410                 415
Arg Ser Ser Leu Leu Ser Val Tyr Ala Asp Met Ser Val Thr Cys Lys
            420             425                 430
Glu Tyr Tyr Asp Pro Asn Arg Ser Met Leu Glu Leu Val Phe Ala Pro
        435             440                 445
Ala Asp Glu Trp Ile Gly Arg Ser Asp Thr Glu Ile Ile Asp Ala Thr
    450             455                 460
Met Glu Glu Leu Ala Lys Leu Phe Pro Asp Glu Ile Ala Ala Asp Gln
465             470                 475                     480
Ser Lys Ala Lys Ile Leu Lys Tyr His Ile Val Lys Thr Pro Arg Ser
            485                 490                 495
Val Tyr Lys Thr Val Pro Asn Cys Glu Pro Cys Arg Pro Leu Gln Arg
            500                 505                 510
Ser Pro Ile Glu Gly Phe Tyr Leu Ala Gly Asp Tyr Thr Lys Gln Lys
        515             520                 525
Tyr Leu Ala Ser Met Glu Gly Ala Val Leu Ser Gly Lys Leu Cys Ala
    530             535                 540
Gln Ser Ile Val Gln Asp Tyr Ser Arg Leu Ala Leu Arg Ser Gln Lys
545             550                 555                     560
Ser Leu Gln Ser Gly Glu Val Pro Val Pro Ser
            565             570
```